United States Patent

Bennett et al.

[11] Patent Number: 4,603,977
[45] Date of Patent: Aug. 5, 1986

[54] MICROMOTILITY METER

[75] Inventors: James L. Bennett, Haslett; Ralph A. Pax, Mason, both of Mich.

[73] Assignee: Research Corporation, New York, N.Y.

[21] Appl. No.: 666,931

[22] Filed: Oct. 31, 1984

[51] Int. Cl.⁴ ............................................. G01N 21/00
[52] U.S. Cl. .................................... 356/436; 356/442; 435/808
[58] Field of Search ............... 356/335, 436, 440, 442, 356/445, 448; 436/164, 805; 435/291, 808

[56] References Cited

U.S. PATENT DOCUMENTS 3,480,369 11/1969 Smythe et al. ...................... 356/440
4,176,953 12/1979 Bartoov et al. ..................... 356/442

*Primary Examiner*—R. A. Rosenberger
*Attorney, Agent, or Firm*—Scully, Scott, Murphy & Presser

[57] ABSTRACT

A micromotility meter for evaluating the movement of helminths in a test solution is provided, including a dark chamber having a test tube holding the solution containing a drug to be tested and a plurality of helminths placed within the solution. The solution defines a meniscus at a side wall of the test tube. A light source is directed upwardly through the test tube and is refracted from the meniscus to a photodetector adjacent the meniscus on the outside of the tube. Movement of the helminths causes a variation of the light rays refracted from the meniscus which results in an amplitude modulated electrical signal emanating from the photodetector that reflects the movement of the helminths. An electronic computation means is responsive to the modulated signal to quantitatively analyze the movement of the helminths and provide an index of motility.

33 Claims, 5 Drawing Figures

MICROMOTILITY METER

BACKGROUND OF THE INVENTION

1. Field of the Invention

This invention relates to an apparatus for and a method of evaluating the movement of helminths in solution and for quantifying that movement.

2. Description of the Prior Art

The problem of infectious diseases caused by helminthic parasites is a major concern of Parasitologists, who are continually developing drugs to fight these diseases. The newly developed drugs must be tested for their effect on the helminthic parasites before the drugs can be marketed. Generally, the tests are performed on several animals having the disease, which can be a costly procedure. Sufficient amounts of the drug must be synthesized to perform these tests and, in addition, it is expensive to purchase and maintain the animals.

It is therefore desirous to perform a prescreening test of the drugs to see if they have any effect on the helminths before testing on the animals. This initial testing can be performed in vitro by removing the helminths from the host animal, such as a rat, and placing the helminths in a solution to which the drug is added. The movement of the helminths in the solution containing the drug can be observed, thereby indicating whether or not the drug has an effect on the helminthic parasites.

At present, the body movement or motility of the helminths is observed by eye. However, there are high numbers of drugs to be tested every day and visual inspection would not be practical to obtain meaningful quantitative data. Several devices are known for automatically measuring the movements of the helminths. In one such device, disclosed in The Journal of Pharmacology and Experimental Therapeutics, Vol. 185, No. 2, 177-184 and The American Journal of Tropical Medicine and Hygiene, Vol. 22, No. 6, 734-742 (1973), a light source passes light through a test cell having a solution containing the helminths and the drug to be tested. The bottom of the cell has several holes in which are connected fiber optic light guides that are also connected to photocells. The movement of the helminths will cause one or more of the fiber optic guides to be intermittently covered and uncovered thereby shutting off and turning on an amplifier connected to each photocell. The number of times the helminths cover and uncover the fiber optic guides is counted and quantified by appropriate computer interface equipment. The fiber optic device is limited since only whole worm movements can be detected and therefore cannot measure the activity of small parasitic helminths.

Another known device is disclosed in Medical and Biological Engineering and Computing, 408-418 (1978), wherein an ultrasonic Doppler effect is utilized to detect the movement of the worms. Frequency shifts caused by the moving worms are recorded and quantified. This ultrasonic measuring apparatus is an expensive, technologically complicated device making it unsuitable for widespread distribution.

The measurement of sperm motility is disclosed in U.S. Pat. No. 4,176,953 issued to Bartoov, et al. In U.S. Pat. No. 4,176,953, a light source and photoelectric cell are aligned on opposite sides of a transparent container containing the suspension of sperm cells. The variations of optical density caused by the collective motion of batches of the sperm cells is detected. The device does not sense individual sperm cells but rather examines a predetermined field of the cell suspension. Thus, the device would not be useful for obtaining an index of motility for small parasitic helminths.

Thus, there is a need for a simple, inexpensive device to obtain quantitative data of the movement of helminths to provide a motility index for studying the effect of newly developed drugs on the helminths.

SUMMARY OF THE INVENTION

It is an object of the present invention to provide an apparatus to accurately quantitate the movement of small parasitic helminths.

It is another object of the present invention to provide an apparatus and method for determining the organism toxicity of a test solution.

In accordance with the present invention, there is provided a micromotility meter including a dark chamber for receiving a transparent container that contains a test solution and a plurality of helminths in the solution. The top surface of the solution is defined by a meniscus at the side wall of the transparent container. A light source is provided within said dark chamber which directs light upwardly through the bottom of the transparent container and up to and through the meniscus. A portion of the light emanating from the light source is refracted by the meniscus at a 90 degree angle and is collected by a photodetector located on the outside of the transparent container adjacent to the meniscus. When no helminths are in the transparent container, the light bombards the photodetector with a constant flux of energy which translates into a constant stable voltage output from the photodetector. When helminths are placed in the bottom of the container, their movement will disturb the flow or flux of the light passing through the container, thereby disturbing the light striking various regions of the meniscus. The variability of the amount of light striking various regions of the meniscus results in a variation of the voltage coming from the photodetector. This variation in voltage is a direct reflection of the muscle or motor activity of the helminths. This variation of voltage is detected and amplified and converted to a digital format by an analog to digital converter and is entered into a computer that will derive an index of motility of the helminths. The apparatus of the present invention can be used as an initial testing procedure for newly developed drugs to counteract small parasites. Only a small amount of the newly developed drug need be synthesized, approximately a few milligrams, which will result in a substantial cost saving. In addition, the present invention provides an automated system for evaluating high numbers of test solutions.

The apparatus of the present invention may also be used to monitor anti-helminthic drugs in animals used for human consumption. In addition, the toxicity of solutions such as contaminated water can be evaluated. The motility of the toxic organisms can be detected and analyzed by placing an extract of the toxic substance in a solution and placing the solution within the transparent container of the device. The toxicity meter would indicate when the variations in the signal emanating from the photodetector has dropped below a predetermined level to indicate that the motility of the organism has ceased.

BRIEF DESCRIPTION OF THE DRAWINGS

The following is a detailed description, together with accompanying drawings of an illustrative embodiment of the invention. It is to be understood that the invention is capable of modification and variation apparent to those skilled in the art within the spirit and scope of the invention.

DETAILED DESCRIPTION OF THE INVENTION

Figure 1:
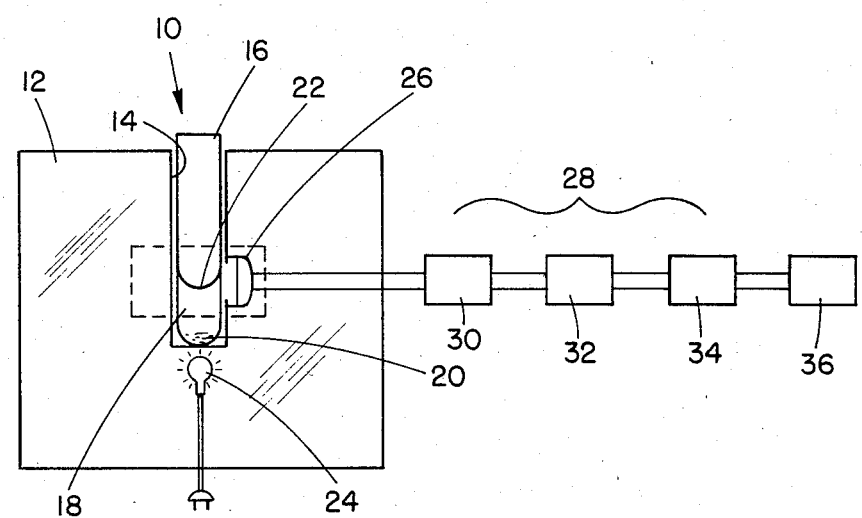
FIG. 1 is an elevational, cross-sectional view of the chamber with the test container therein and a block diagram of the electrical system.

Referring now to the drawings, there is shown a micromotility meter 10 including a housing 12 made of ebonite or other dark material having a dark chamber 14 for receiving a transparent container or cruet 16, such as a test tube. The test tube 16 contains a medium of a test solution 18 in which is placed a plurality of helminths 20. The top surface of the test solution defines a meniscus 22.

A light source 24, preferably a microlight, is located within the housing 12, and when lit, directs light upwardly from the bottom of the test tube 16 through the solution 18 along the longitudinal axis of the test tube 16. A photodetector means 26 is located within the housing 12 adjacent to the meniscus 22 for collecting light refracted by the meniscus 22. The solution 18 contains the drug to be tested which contacts the helminths 20 placed in the test tube 16. The movement of the helminths 20 will cause variations in the light refracted by the meniscus 22. The photodetector means 26 converts the variation in the refracted light to an amplitude modulated electrical signal that is received by an electronic computation means 28 responsive to the modulated signals to provide an index of motility of the helminths.

The micromotility meter 10 can evaluate the effect a drug has on the activity of various helminthic parasites. However, by utilizing the light refracted from the meniscus 22 which extends across the entire cross section of the test tube 16, the present invention is uniquely suited for testing the various small parasitic helminths from as small as 30 microns in length. The helminthic parasites that can be tested includes for example, *Nippostrongyloide brasiliensis, Harmonchus contortus, Synrhabdihs elegans, Caenorhabditis elegans, Diroplaria immihs* and *Schistosoma manseni*. These parasites range from 30 microns to 3 mm in length and from 10 microns to 300 microns wide.

Generally, 20-50 helminths are placed in 50 microliters of test solution 18. To accommodate the various helminths 20, the test tube 16 will have a diameter any where between 2.5 mm to 2.5 cm so that the helminths 20 will occlude at least 10 to 25% of the cross-sectional area of the test tube 16. The drug concentrations that can be detected are generally in the range of one part per million, and with certain drug activity to one to ten parts per billion.

The helminths 20 may be cultivated in the test solution 18 for 24 hours before testing. However, the motility index may be obtained even if the helminths 20 are tested within as little as one minute after being placed in the test solution 18.

Figure 5:
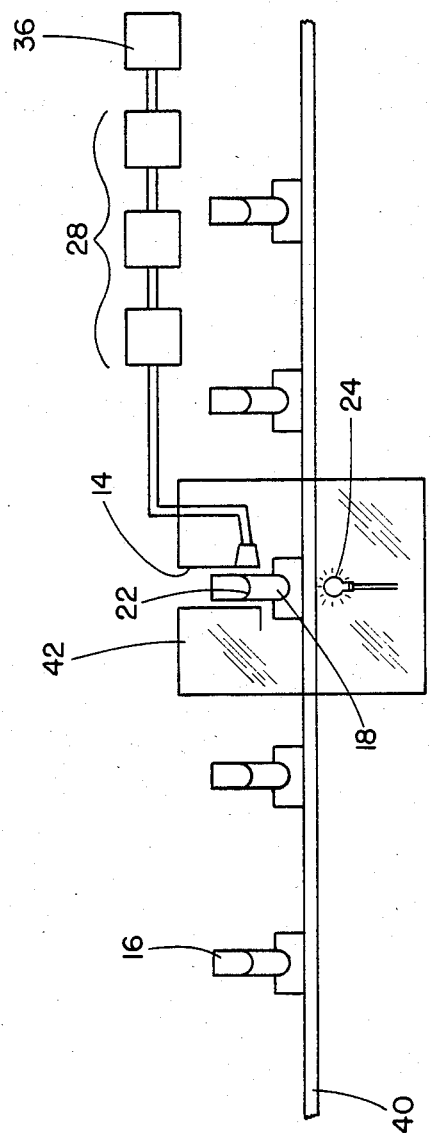
FIG. 5 is a schematic of the conveyor system of the invention.

In a preferred embodiment a conveyor 40 is provided to intermittently transport a plurality of transparent containers 16 holding the helminths 20 through the chamber 14 in order to test a single drug on various parasites at the same time, or to test high numbers of test solutions, as shown in FIG. 5.

The electronic computation means 28 includes an amplifier 30 that amplifies the signal coming from the photodetector 26 and a threshold means 32 that selects variations of the amplified signal beyond a predetermined level as indicative of a movement event. A counter 34 counts the number of movement events coming from the output of the threshold means 32 over a period of time to provide a motility index. The threshold means 32 includes an analog to digital converter which also categorizes the various levels of amplitude coming from the amplifier 30 at different activity levels. In this case, the counter 34 counts the number of activity levels to provide the motility index. The motility index can also be determined from a frequency histogram obtained by counting the number of events for each level for a predetermined period of time. A computer 36 stores the index of motility and correlates a specific container 16 with the corresponding index.

Figure 2:
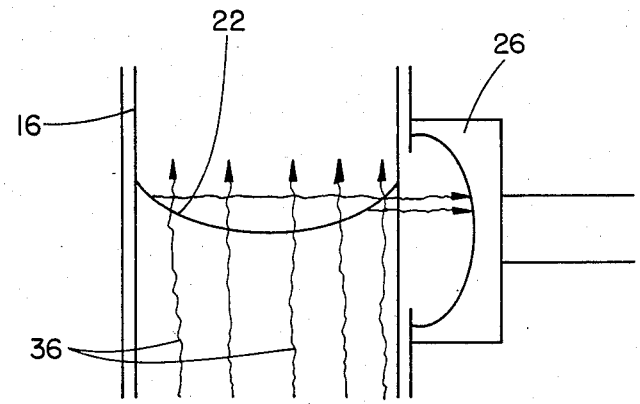
FIG. 2 is an enlarged view of the area of the chamber showing the meniscus and the refracted light waves.
Figure 3:
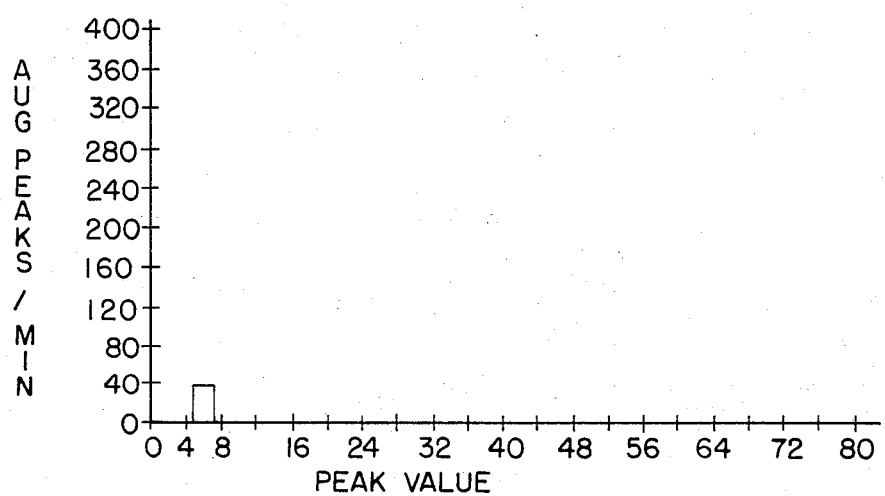
FIG. 3 is a graph showing the digital output of photodetector when no helminths are in the test container.

If the device is operated with no helminths in the test tube 16, the light rays 38, as shown in FIG. 2, will be partially refracted from the meniscus 22 with a constant flux of energy which will translate into a constant voltage output from the photodetector. As shown in the graph in FIG. 3, the output voltage averages 40 peaks per minute at a peak value of approximately 6 mv. When the helminths 20 are placed in the bottom of the test tube 16, they will disturb the flow of the light rays 38 passing through the tube 16. Thus, the distribution of light striking the various regions of the meniscus 22 will be varied and the amount of light refracted by the meniscus 22 will be correspondingly varied. The variability of the amount of light results in a variation of the voltage coming from the photodetector 26 which is a direct reflection of the muscle or motor activity of the helminths 20. This variation of voltage is passed through the electronic computation means 28 which results in various digital signals corresponding to the motility index.

Figure 4:
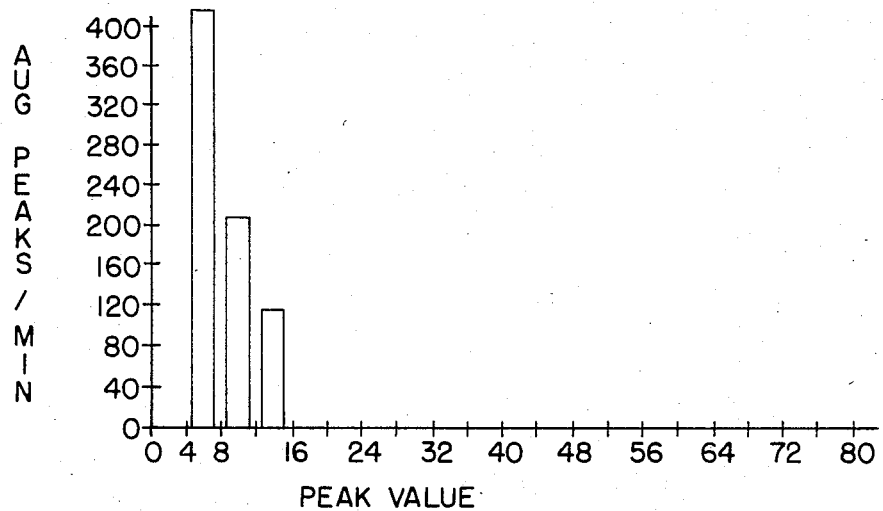
FIG. 4 is a graph showing the variation of the output of the photodetector caused by the movement of helminths in the test container.

FIG. 4 shows the results when approximately 50 helminths were placed within the test tube 16, approximately 6 by 50 mm, containing 50 microliters of solution 18. Here, the variation of the amplitude of the signal emanating from the photodetector can be seen as compared to the steady flow shown in FIG. 3 when no worms are present. Peak values are detected in the 6, 8 and 12 mv range, averaging 460, 200 and 120 peaks per minute, respectively. Thus, quantitative data is easily available by using the present invention.

The present invention may also be used as a toxicity meter for evaluating the toxicity of an unknown solution. In this embodiment, a plurality of motile organisms, such as protozoa, are placed within the solution 18. The solution 18 is placed in the test tube 16 which is inserted within the dark chamber 14. The light source 24 directs light upwardly through the meniscus 22 of the solution 18 and is refracted thereby into the photodetector 26. The electronic computing means 28 indicates when the variations in the signal emanating from the photodetector 26 has dropped below a predetermined level which indicates that the motility of the organisms has ceased. Thus, antihelminthics extracted from organs of various food animals can be detected for approved levels for human consumption. In addition, the effects of potential toxic or contaminated water may also be tested by the toxicity meter of the present invention.

As shown in FIG. 5, a large number of unkown test solutions 18 can be tested for helminthic toxicity by intermittently conveying a plurality of test containers 16, each having a separate test solution containing a plurality of the helminths 20, past a measuring station 42 for a predetermined period of time. At the measuring station 42, the light source 24 is directed upwardly through the test solution 18 to strike the meniscus 22 formed at the top surface of the solution. The light is refracted by the meniscus 22 and the variations in the refracted light over the period of time is generated into a helminth toxicity signal when the amplitude of the variations drops below the predetermined level. The toxicity signal is generated by the electronic means 28 described earlier.

Generally, the conveyor means 40 will be adapted to present each test container 16 at the measuring station 42 for at least 30 seconds so that a representative signal can be generated. The data derived by the electronic computation means 28 is correlated to each test solution 18 and stored in the computer 36. Thus, the present invention permits quantitative data to be easily obtained and evaluated for large numbers of test solutions thereby greatly increasing testing productivity.

While illustrative embodiments of the subject invention have been described and illustrated, it is obvious that various changes and modifications can be made therein without departing from the spirit of the present invention which should be limited only by the scope of the appended claims.

What is claimed is:

1. A micromotility meter for evaluating the movement of helminths in solution, said meter comprising:
    (a) a dark chamber for receiving a transparent container containing a test solution and a plurality of helminths in said solution, said solution defining a meniscus at a side wall of the container,
    (b) a light source for directing light upwardly through said solution meniscus,
    (c) photodetector means for collecting light refracted by said meniscus, said photodetector means generating a first signal that is modulated by variations in the refracted light caused by movement of the helminths,
    (d) means responsive to said modulated first signal to provide an index of motility of the helminths.

2. A micromotility meter as claimed in claim 1 which further includes:
    (a) an intermittent conveyor means for transporting a plurality of transparent containers through said dark chamber, each container having a plurality of helminths in a test solution therein,
    (b) means for storing an index of motility for each container evaluated in said dark chamber,
    (c) control means for correlating a specific container with the index motility recorded for that container.

3. A micromotility meter as claimed in claim 1 or 2 wherein said responsive means further comprises a threshold means for selecting variations in the amplitude of said first signal beyond the predetermined level as indicative of a movement event for said index.

4. A micromotility meter as claimed in claim 3 which further includes a counter for counting the number of movement of events over a period of time to provide a motility index.

5. A micromotility meter as claimed in claim 1 or 2 wherein said responsive means further includes means for measuring the amplitude of said variations and categorizing various levels of amplitude at different activity event levels, said responsive means also including a counter for counting the number of activity events at each level of activity for a predetermined period of time.

6. A micromotility meter as claimed in claim 5 wherein an analog to digital converter categorizes various levels of amplitude at different activity levels.

7. A micromotility meter as claimed in claim 1 or 2 wherein said transparent container is a transparent cruet having a diameter between 2.5 mm. and 2.5 cm.

8. A micromotility meter as claimed in claim 1 or 2 wherein said transparent container contains helminths from 30 microns to 3 mm. in length.

9. A micromotility meter as claimed in claim 7 wherein 20 to 50 helminths are placed in 50 microliters of test solution.

10. A method of measuring the motility of helminths in a test solution, said method comprising:
    (a) introducing a plurality of helminths into a transparent container having a test solution therein,
    (b) directing a light upwardly through said solution to strike a meniscus formed between the solution and the transport container,
    (c) measuring the light refracted from said meniscus to detect variations in refracted light caused by movement of the helminths,
    (d) generating a motility index based on the variations in the refracted light.

11. A method of measuring motility of helminths as claimed in claim 10 which further includes the step of converting the measurements obtained from the variations in refracted light to digital signals.

12. A method of measuring the motility of helminths as claimed in claim 10 wherein the step of generating a motility index further includes the steps of:
    (a) converting the variations in refracted light to amplitude modulated electrical signals,
    (b) categorizing the variations and amplitude into a series of discrete event levels,
    (c) counting the number of events for each level for a predetermined period of time to obtain a frequency histogram.

13. A method of measuring the motility of helminths as claimed in claim 10 wherein said helminths occlude from 10 to 25% of the cross-sectional area of the transparent container.

14. A toxicity meter for evaluating an unknown test solution for organism toxicity, said meter comprising:
    (a) a dark chamber for receiving a transparent container containing a test solution and a plurality of motile organisms in said solution, said solution defining a meniscus at a side wall of the container,
    (b) a light source for directing light upwardly through said solution meniscus, (c) a photodetector means for collecting light refracted by said meniscus, said detector means generating a first signal that is modulated by variations in the refracted light caused by movement of the motile organisms, (d) a measuring means responsive to said modulated first signal to provide an index of motility of the organisms, (e) toxicity detector means for indicating when the variations in said first signal have dropped below a predetermined level, thereby indicating the motility of the organisms has ceased.

15. A toxicity meter as claimed in claim 14 which further includes:

(a) an intermittent conveyor means for transporting a plurality of transparent containers through said dark chamber, each container having a plurality of motile organisms in a test solution therein, (b) means for storing an index of motility for each container evaluated in said dark chamber, (c) control means for correlating a specific container with the index motility recorded for that container.

16. A toxicity meter as claimed in claim 14 or 15 wherein said responsive means further comprises a threshold means for selecting variations in the amplitude of said first signal beyond the predetermined level as indicative of a movement event for said index.

17. A toxicity meter as claimed in claim 16 which further includes a counter for counting the number of movement events over a period of time to provide a motility index.

18. A toxicity meter as claimed in claim 14 or 15 wherein said responsive means further includes means for measuring the amplitude of said variations and categorizing various levels of amplitude at different activity event levels, said responsive means also including a counter for counting the number of activity events at each level of activity for a predetermined period of time.

19. A toxicity meter as claimed in claim 18 wherein an analog to digital converter categorizes various levels of amplitude at different activity levels.

20. A toxicity meter as claimed in claim 14 or 15 wherein said transparent container is a transparent cruet having a diameter between 2.5 mm. and 2.5 cm.

21. A toxicity meter as claimed in claim 14 or 15 in which 20 to 50 motile organisms are placed in 50 microliters of test solution.

22. A toxicity meter as claimed in claim 14 or 15 wherein the motile organisms are helminths ranging from 30 microns to 3 millimeters in length.

23. A toxicity meter as claimed in claim 14 or 15 in which the motile organisms are motile protozoa.

24. A method of measuring the toxicity of an unknown test solution, said method comprising:

(a) introducing a plurality of living motile organisms into an unknown test solution in a transparent container, (b) directing a light upwardly through said solution to strike a meniscus formed between the solution and the transparent container, (c) measuring the light refracted from said meniscus to detect variations of refracted light caused by movement of the motile organisms, (d) generating a toxicity signal when the variations in the amplitude of said signal drops below a predetermined level.

25. A method of measuring the toxicity of an unknown solution as claimed in claim 24, wherein the step of generating a toxicity signal further includes the step of converting the measurements obtained from the variations in refracted light to digital signals with an analog to digital converter.

26. A method of measuring the toxicity of an unknown solution as claimed in claim 24 wherein 20 to 30 motile organisms are placed in 50 microliters of test solution.

27. A method of measuring the toxicity of an unknown solution as claimed in claim 24 wherein the motile organisms are helminths ranging from 30 microns to 3 millimeters in length.

28. A method of measuring the toxicity of an unknown solution as claimed in claim 24 wherein the motile organisms are motile protozoa.

29. A method of automatically testing a large number of test unknown solutions for helminths toxicity, said method comprising:

(a) introducing each test solution into a separate transparent container, said containers having a plurality of helminths therein, (b) intermittently conveying each container past a measuring station wherein each container is evaluated for a predetermined period of time, (c) directing a light upwardly through said solution to strike a meniscus formed between the unknown solution and side wall of the container, (d) generating a motility index based on the measured variations in the refracted light over said period of time, (e) correlating the motility index to the unknown sample conveyed through said measuring station.

30. A method of automatically testing a large number of test solutions as claimed in claim 29 which further includes the step of generating a helminth toxicity signal when the amplitude of said measured variations drops below a predetermined level.

31. A method of automatically testing a large number of test solutions as claimed in claim 29 wherein said step of generating a motility index further includes the steps of:

(a) categorizing the variations in amplitude of said measured variations into a series of discrete event levels, (b) counting the number of events for each applicable event level for a predetermined period of time to obtain a frequency histogram.

32. A method of automatically testing a large number of test solutions as claimed in claim 29 wherein said helminths range from 30 microns to 3 millimeters in length.

33. A method of automatically testing a large number of test solutions as claimed in claim 29 wherein 20 to 30 helminths are placed in approximately 50 microliters of each test solution.

* * * * *